United States Patent [19]
Plattner et al.

[11] 4,219,497
[45] Aug. 26, 1980

[54] CHROMOGENIC SUBSTRATES

[75] Inventors: Jacob J. Plattner; Stephen D. Stroupe; Houston F. Voss, all of Libertyville, Ill.

[73] Assignee: Abbott Laboratories, North Chicago, Ill.

[21] Appl. No.: 27,578

[22] Filed: Apr. 6, 1979

[51] Int. Cl.$^2$ .................. C07C 103/87; C07C 129/12
[52] U.S. Cl. ........................... 260/501.14; 260/558 S; 260/559 D; 260/559 T; 260/558 P; 260/556 AR; 260/326 S; 560/16
[58] Field of Search ........... 260/558 S, 559 D, 559 T, 260/501.12, 501.14

[56] References Cited
U.S. PATENT DOCUMENTS
4,070,245  1/1978  Svendsen ............................... 195/99

FOREIGN PATENT DOCUMENTS
2322115  11/1973  Fed. Rep. of Germany .
2322116  11/1973  Fed. Rep. of Germany .
2527932   1/1976  Fed. Rep. of Germany .

OTHER PUBLICATIONS
Fok et al., Biochem. and Biophys. Res. Comm., vol. 74, No. 1, pp. 273-278 (1977).

Primary Examiner—Thomas A. Waltz
Attorney, Agent, or Firm—John J. McDonnell

[57] ABSTRACT

The present invention comprises compounds of the formula

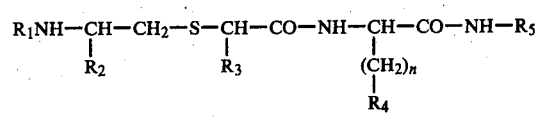

and the biologically acceptable acid addition salts thereof wherein $R_1$ represents hydrogen, or lower alkyl having 1-4 carbon atoms; $R_2$ represents p-hydroxybenzyl or benzyl; $R_3$ represents an alkyl having 1-6 carbon atoms; $R_4$ represents amino or guanidino; $R_5$ represents p-nitrophenyl, methylnitrophenyl, dinitrophenyl, naphthyl, or nitronaphthyl; and n is 3 or 4.

4 Claims, No Drawings

CHROMOGENIC SUBSTRATES

BACKGROUND OF THE INVENTION

The present invention relates to reagents useful in the quantitative determination of proteolytic enzymes. More particularly the present invention relates to peptide derivatives which are substrates for enzymes of the class E.C.3.4.4. These enzymes cleave amide linkages in peptide chains on the carbonyl side of arginine and lysine residues.

Classical substrates for trypsin, thrombin, and related enzymes have involved amides such as $N^\alpha$-benzoyl-DL-arginyl-p-nitroanilide, L-lysyl-p-nitroanilide, $N^\alpha$-benzoyl-DL-arginyl-2-naphthylamide and other di, tri, and higher order arginine and lysine peptides with chromogenic amide leaving groups [B. F. Erlanger, et al., Arch. Biochem. Biophys., 95, (1961) 271; A. Riedel and E. Wunsch, Z. Physiol. Chem., 316, (1961) 1959; R. E. Plapinger, et al., J. Org. Chem., 30 (1965) 1781; L. Svendsen, et al.].

The advantage of extending the amino terminal end of either arginyl or lysyl-p-nitroanilide substrates results in improved substrate behavior [Thrombosis Res., 1, (1972) 267–78; U.S. Pat. No. 3,884,896], and in particularly, a number of prior art disclosures describes various p-nitroaniline derivatives of tripeptides or higher peptides [U.S. Pat. Nos. 4,070,245; 4,061,625; and 4,016,042].

The present invention reagents are p-nitroaniline derivatives of dipeptides containing a thiomethylene group in place of a peptide linkage. Thiomethylene substituted for the peptide linkage between glycine and leucine in a compound of the formula (S)-2-(S-cysteaminyl)-4-methylpentoic acid is described by K. F. Fok and J. A. Yankeelov, Jr., [Biochem. and Biophys. Res. Comm., 74, 273 (1977)] with the resulting thiomethylene substituted peptide active as an effective inhibitor of aminopeptidase M. The invention reagents, however, are structurally different and act as effective substrates for proteolytic enzymes rather than as enzyme inhibitors.

BRIEF DESCRIPTION OF THE INVENTION

The present invention comprises compounds of the formula

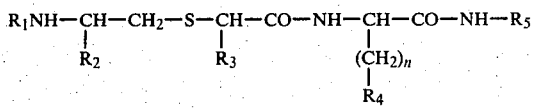

and the biologically acceptable acid addition salts thereof wherein $R_1$ represents hydrogen or lower alkyl having 1–4 carbon atoms; $R_2$ represents p-hydroxybenzyl or benzyl; $R_3$ represents an alkyl having 1–6 carbon atoms; $R_4$ represents amino or guanidino; $R_5$ represents p-nitrophenyl, methylnitrophenyl, dinitrophenyl, naphthyl, or nitronaphthyl; and n is 3 or 4.

The present invention relates to analytical reagents useful for measuring proteolytic enzymes such as thrombin and trypsin. The enzymatic hydrolysis of the invention reagents provides a chromogenic amine by which the proteolytic enzyme concentration can be determined spectrophotometrically.

DETAILED DESCRIPTION OF THE INVENTION

The present invention encompasses compounds represented by the formula

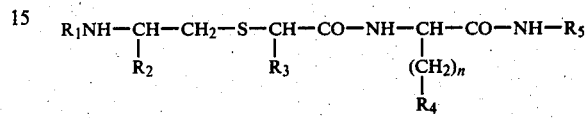

and the biologically acceptable acid addition salts thereof as previously defined, $R_1$ represents hydrogen or lower alkyl having 1–4 carbon atoms as exemplified by methyl, ethyl, propyl, isopropyl or butyl; $R_2$ represents p-hydroxybenzyl or benzyl; $R_3$ represents an alkyl having 1–6 carbon atoms; $R_4$ represents amino (where L-lysine or L-ornithine is used) or guanidino (where arginine is used); n represents, thereby, 3 or 4 corresponding to the use of either L-arginine or L-ornithine (where n equals 3) or L-lysine (where n equals 4); and $R_5$ is selected from the group consisting of nitrophenyl, methylnitrophenyl, dinitrophenyl, naphthyl and nitronaphthyl. Preferrably $R_5$ is nitrophenyl. The chemical art recognizes biologically acceptable chromogenic substitutes for nitrophenyl [Plapinger, Nachlas, Seligman, and Seligman, J. Organic Chemistry, 30, 1781, (1965); U.S. Pat. No. 3,884,896].

Preferred reagents are biologically acceptable acid addition salts of compounds of the formula

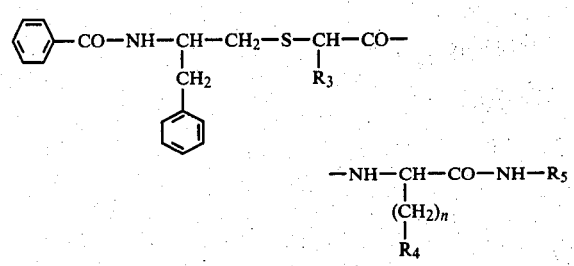

wherein $R_3$, $R_4$, $R_5$ and n are as previously defined.

The most preferred reagents are biologically acceptable acid addition salts of compounds of the formula

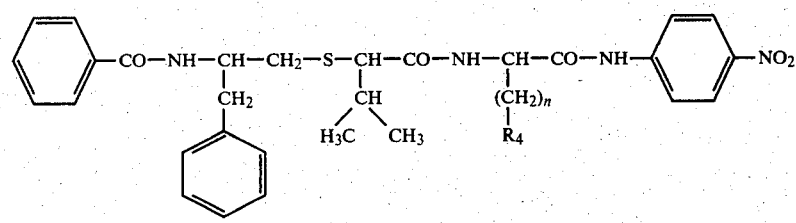

wherein $R_4$ and n are as previously defined.

The various chromogenic reagents of the present invention are prepared by the following scheme:

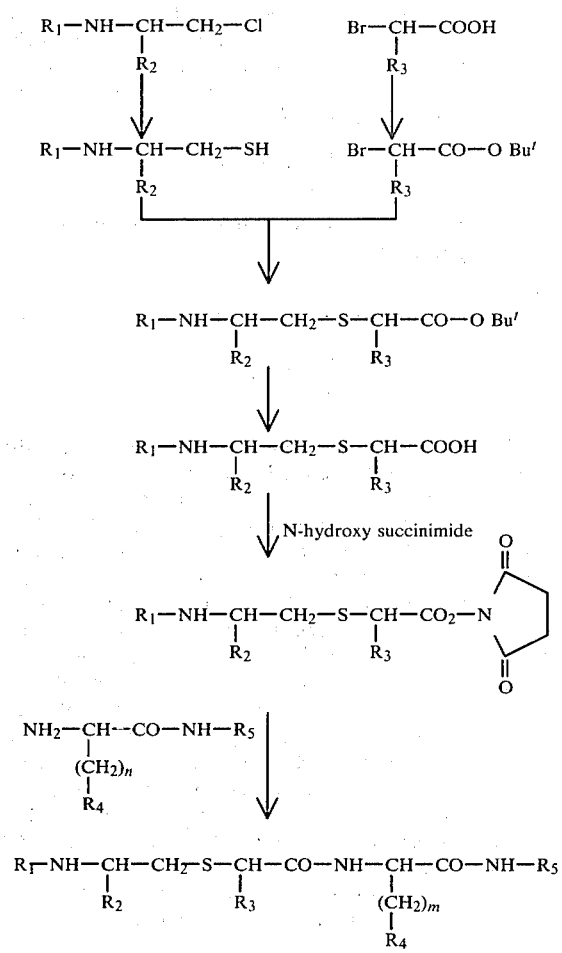

Typically, 3-phenyl-2-benzamido-1-chloropropane of the formula

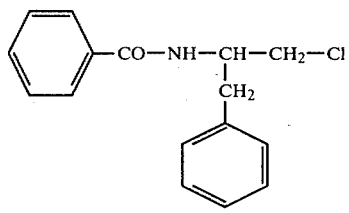

is synthesized from L-phenylalanine as described by K. Koga, et al., *Chem. Pharm. Bull.*, 14, 243 (1966). 3-Phenyl-2-benzamido-1-chloropropane is reacted with thiourea and then with aqueous sodium hydroxide to provide 3-phenyl-2-benzamido-1-propanethiol of the formula

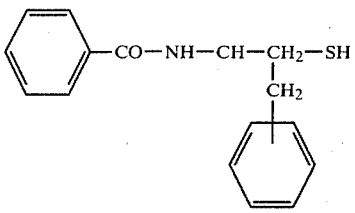

(+)-2-Bromo-3-methylbutyric acid is synthesized from D-valine as described by Gaffield and Galetto, *Tetrahedron*, 27, 915 (1971) and reacted with isobutylene in acid solution to provide (+)-t-butyl 2-bromo-3-methylbutyrate. This product is reacted under anhydrous conditions with the lithium salt of 3-phenyl-2-benzamido-1-propanethiol to provide t-butyl 3-methyl-2-(3-phenyl-2-benzamidothiopropyl)butyrate of the formula

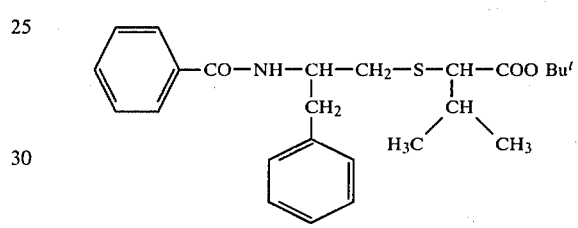

This latter product is submitted to a methylene chloride and trifluoroacetic acid solution to remove the t-butyl ester and provide 3-methyl-2-(3-phenyl-2-benzamidothiopropyl)butyric acid. This acid is activated for coupling by conversion to 3-methyl-2-(3-phenyl-2-benzamidothiopropyl)butyric acid N-hydroxysuccinimide ester of the formula

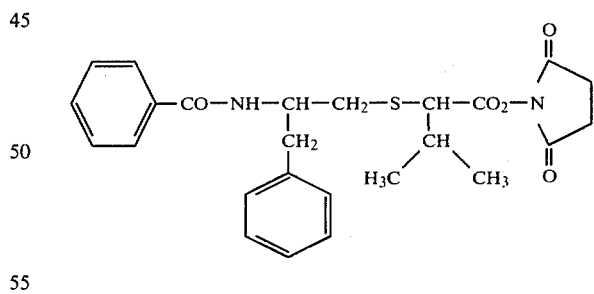

Carbobenzoyl-L-arginyl(methoxybenzenesulfonyl)-p-nitroanilide is prepared by reacting carbobenzoxyl-L-arginyl (methoxybenzenesulfonyl)-p-nitroanilide with p-nitrophenylisocyanate. Subsequently, carbobenzoxy is removed and the resulting product is coupled with 3-methyl-2-(3-phenyl-2-benzamidothiopropyl)butyric acid N-hydroxy succinimide ester to provide $N^\alpha$-(3-methyl-2-(3-phenyl-2-benzamidothiopropyl)-butanoyl)-L-arginyl(methoxybenzenesulfonyl)-p-nitroanilide of the formula

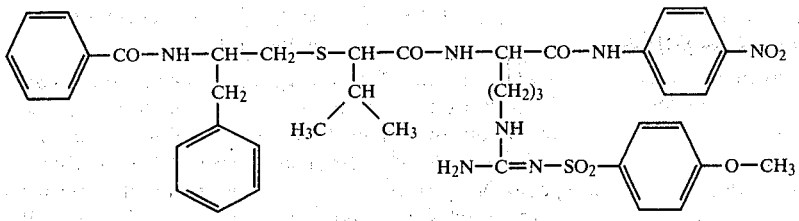

The methoxybenzenesulfonyl moiety is removed by submitting the above product to anhydrous hydrogen fluoride, thereby providing $N^\alpha$-[3-methyl-2-(3-phenyl-2-benzamidothiopropyl) butanoyl]-L-arginyl-p-nitroanilide hydrogen fluoride of the formula

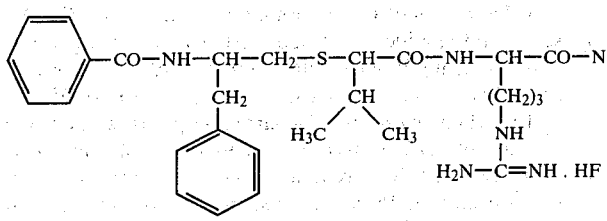

TABLE I

| Thrombin | | Trypsin | |
|---|---|---|---|
| $k_{cat}$ sec$^{-1}$ | $K_m$ X10$^{-4}$M | $k_{cat}$ sec$^{-1}$ | $K_m$ X10$^{-2}$M |
| 58 | 6 | 305 | 1 |

Carbobenzoxy and methoxybenzenesulfonyl act as amino protecting groups in generating the above products. These protecting groups may be replaced by other groups such as t-butyloxycarbonyl, O-nitrophenylsulfonyl, and tosyl. Those skilled in peptide synthetic art will recognize a wide variety of synthetic approaches to peptides of this kind.

The chromogenic reagents of this invention encompass biologically acceptable acid addition salts of compounds whose salts have been prepared from mineral acids such as hydrochloric, hdyrobromic, sulfuric, nitric, phosphoric, or from organic acids such as formic, acetic, tartaric, methanesulfonic and benzenesulfonic. Those skilled in the art will recognize the equivalence of other organic and mineral acids.

In a typical procedure using the chromogenic reagents of the invention, the enzyme, such as trypsin or thrombin, and the substrate are mixed in a buffer solution and the reaction is followed spectrophotometrically. The concentration of the substrate is varied, while the enzyme concentration is kept constant. As is well-known in the art, a plot of the optical density as a function of time gives a curve from which the rate of reaction can be determined. Correspondingly, a Lineweaver-Burk plot therefrom permits determination of $K_m$ and $k_{cat}$.

Table I presents Michaelis-Menton kinetic data and illustrates the usefulness of $N^\alpha$-[3-methyl-2-(3-phenyl-2-benzamidothiopropyl)-butanoyl]-L-arginyl-p-nitroanilide of this present invention for determining thrombin and trypsin. The kinetic data was obtained from reactions run in 0.17 M TRIS at pH 7.4. The reaction mixture contained highly purified bovine trypsin at $3.33 \times 10^{-8}$ M or highly purified human thrombin at $2.09 \times 10^{-8}$ M and 50 liters of $N^\alpha$-[3-methyl-2-(3-phenyl-2-benzamidothiopropyl)butanoyl]-L-arginyl-p-nitroanilide which has been obtained by dissolving 14 mg of the thiomethylene substrate in 4 ml ethanol-water (75:25 ratio) and diluting 1:400 with TRIS buffer. The reaction was analyzed on a Varian Superscan at 406 nm and 37° C.

Clinically, the chromogenic substrates are used to measure antithrombin III.

Antithrombin III (AT-III) is the major component of the anticoagulation system. It inhibits a variety of serine proteases by forming a 1:1 complex via serine, the active center of such enzymes. The presence of heparin increases the rate of reaction of AT-III with such proteases approximately 100-fold, making AT-III the only plasma component involved in this rapid inhibition reaction.

The chemistry of the AT-III is described in the following equations:

Thrombin + AT-III $\xrightarrow{\text{Heparin}}$ (Thrombin:AT-III) + Thrombin excess Substrate $\xrightarrow{\text{Thrombin excess}}$ Peptide + p-nitroaniline (yellow-greem chromophore)

Since the presence of heparin potentiates the activity of AT-III, it is possible to delineate the inhibition due to AT-III from that of other plasma proetins which can also inhibit thrombin. Thus, one measures total AT-III activity as an entity distinct from the "progressive antithrombin activity" which is measured in the absence of heparin. As a result, one can clearly identify a defect in the anticoagulation system as one associated with AT-III rather than other protein inhibiting mechanisms.

This test relies on the fact that human AT-III in a specimen inhibits human α-thrombin in a 1:1 molar ratio. Excess thrombin is free to hydrolyse a colorless chromogenic substrate. When this substrate is cleaved, it releases, for example, in the absorbance spectrum shown by the development of a yellow-green color. This cleavage of the substrate is analogous to the cleave of the arginyl-glycine bond in fibrinogen which results in the formation of fibrin. By monitoring the color development of the reaction mixture, one can follow the course of the turnover of substrate by thrombin. Since the amount of AT-III and the amount of color produced are inversely proportional, the level of AT-III can readily be determined.

The following examples illustrate the present invention and are not intended to limit the invention in scope or spirit.

EXAMPLE I 3-phenyl-2-benzamido-1-propanethiol 80.4 millimole (mm) of 3-phenyl-2-benzamido-1-chloropropane and 80.4 mm of thiourea are dissolved in 300 ml of ethanol. The resulting solution is refluxed for three hours. 6.7 g of sodium hydroxide is dissolved in 40 ml of water and is added under an inert atmosphere to the solution which is thereafter refluxed for an additional 2½ hours. The solution is then cooled and acidified to pH 1 with 1 N HCl. The resulting mixture is then poured over ice to yield a precipitate which is collected by filtration and then dissolved in chloroform. The chloroform is dried with magnesium sulfate and then evaporated to yield the solid 3-phenyl-2-benzamido-1-propanethiol.

EXAMPLE II (+)-t-butyl 2-bromo-3-methylbutyrate 4.0 mm of (+)-2-bromo-3-methylbutyric acid is dissolved in a solvent consisting of 100 ml of ether, 100 ml of isobutylene, and 0.5 ml of sulfuric acid. The resulting solution is shaken for approximately 72 hours in an autoclave at room temperature. The solution is then neutralized with sodium bicarbonate, dried with magnesium sulfate, and then evaporated to yield (+)-t-butyl 2-bromo-3-methylbutyrate.

EXAMPLE III t-butyl 3-methyl-2-(3-phenyl-2-benzamidothiopropyl)butyrate 96 mm of 3-phenyl-2-benzamido-1-propanethiol is dissolved under an inert atmosphere in 15 ml of tetrahydrofuran. The resulting mixture is collected at −40° C. Thereafter 81.5 mm of n-butyl lithium in 5.1 ml of hexane is added to the mixture, and this solution is then added to 10.5 mm of t-butyl-2-bromo-3-methylbutyrate in 2 ml of tetrahydrofuran. The mixture is then stirred for approximately 15 minutes and then extracted with methylene chloride. The organic phase is collected, dried with magnesium sulfate and evaporated to yield an oil. The oil is chromatographed on a silica gel column, eluting with ethyl acetate-benzene in a ratio of 1:4. Fractions from the column yield t-butyl 3-methyl-2-(3-phenyl-2-benzamidothiopropyl)butyrate.

EXAMPLE IV 3-methyl-2-(3-phenyl-2-benzamidothiopropyl)butyric acid

To a solution of 21.1 mm t-butyl 3-methyl-2-(3-phenyl-2-benzamidothiopropyl)butyrate in 5 ml of methylene chloride is added 15 ml of trifluoroacetic acid. The solution is stirred at room temperature for approximately 2½ hours. The solvent is then evaporated, yielding 3-methyl-2-(3-phenyl-2-benzamidothiopropyl)butyric acid.

EXAMPLE V n$^\omega$-(4-methoxybenzenesulfonyl)-L-arginyl-p-nitroanilide.HBr 23.0 g of N$^\alpha$-carbobenzoxy-N$^\omega$-(4-methoxybenzenesulfonyl)-L-arginine is dissolved in 100 ml of hexamethylphosphoramide. To the resulting solution is added 6.7 ml of triethylamine and 15.8 g of p-nitrophenylisocyanate. The solution is stirred at room temperature overnight and then poured into 1,300 ml of 5% sodium bicarbonate. The resulting precipitate is collected by a filtration funnel and washed separately with (2×400 ml) 5% sodium bicarbonate, (1×300 ml) water, (3×300 ml) 1 N hydrochloric acid and then (2×200 ml) water. The precipitate is dried in the filtration funnel by vacuum suction and then extracted with (3×300 ml) boiling methanol. The methanol extracts are combined and the methanol is evaporated in vacuo at 35° C. The semi-solid residue is purified further by a silica gel column using methylene chloride:methanol (94:5) as eluent. This procedure provides N$^\alpha$-carbobenzoxy-N$^\omega$-(4-methoxybenzenesulfonyl)-L-arginine-p-nitroanilide. 6.0 g of this material is dissolved in 30% hydrobromic acid in acetic acid. The reaction mixture is kept at room temperature for 45 minutes and then poured into 400 ml of dry ether. The precipitated salt is filtered, washed with (2×100 ml) of dry ether and dried in vacuo to provide N$^\omega$-(methoxybenzenesulfonyl)-L-arginine-p-nitroanilide hydrobromide.

EXAMPLE VI 3-methyl-2-(3-phenyl-2-benzamidothiopropyl)butyric acid N-hydroxysuccinimide ester A solution containing 3.87 mm of 3-methyl-2-(3-phenyl-2-benzamidothiopropyl)butyric acid and 5.03 mm N-hydroxysuccinimide is prepared in 25 ml tetrahydrofuran. The resulting mixture is cooled to 0° C. in an ice bath. 5.03 mm of dicyclohexylcarbodiimide in 10 ml tetrahydrofuran is added to the mixture which thereafter is stirred at room temperature overnight. The mixture is filtered and the filtrate collected and evaporated to dryness in vacuo. The resulting residue is dissolved in 20 ml ethyl acetate, washed with aqueous bicarbonate, and then with water, and thereafter dried with sodium sulfate. Evaporation in vacuo of the ethyl acetate provides 3-methyl-2-(3-phenyl-2-benzamidothiopropyl)butyric acid N-hydroxysuccinimide ester.

EXAMPLE VII

N$^\alpha$-[3-methyl-2-(3-phenyl-2-benzamidothiopropyl)-butanoyl]-N$^\omega$-(4-methoxybenzenesulfonyl)-L-arginyl-p-nitroanilide 2.14 mm of N$^\omega$-(4-methoxybenzenesulfonyl)-L-arginyl-p-nitroanilide hydrobromide is dissolved in 2 ml dimethylformamide to which triethylamine is added until the mixture is immediately basic to litmus. The resulting triethylamine hydrobromide precipitate is filtered. The filtrate is collected in a round bottom flask to which 2.14 mm of 3-methyl-2-(3-phenyl-2-benzamidothiopropyl)butyric acid N-hydroxysuccinimide ester is added and allowed to react for approximately 24 hours under an inert atmosphere at room temperature. The dimethylformamide is evaporated in vacuo and the residue is partitioned between ethyl acetate and water. The ethyl acetate phase is collected, dried with magnesium sulfate and evaporated to yield an oil. This oil is column chromatographed over 150 g of silica gel using as eluting solvent of 5% methanol in methylene chloride. This procedure provides $N^\alpha$-[3-methyl-2-(3-phenyl-2-benzamidothiopropyl)-butanoyl]-$N^\omega$-(4-methoxybenzenesulfonyl)-L-arginyl-p-nitroanilide.

EXAMPLE VIII $N^\alpha$-[3-methyl-2-(3-phenyl-2-benzamidothiopropyl)-butanoyl]-L-arginyl-p-nitroanilide.acetic acid salt 0.165 mm of $N^\alpha$-[3-methyl-2-(3-phenyl-2-benzamidothiopropyl)-butanoyl]-$N^\omega$-(4-methoxybenzenesulfonyl)-L-arginyl-p-nitroanilide is reacted with 10 ml of hydrogen fluoride for one hour at 0° C. in a Sakakibara Hydrogen Fluoride Reaction Apparatus as described in U.S. Pat. No. 4,070,245. The reaction product is washed with anhydrous ether which is then removed by decanting, leaving the product residue in the reaction vessel. The product residue is dissolved in 60% methanol (aqueous), filtered and chromatographed on 20 ml of Bio-Rad AGX1 (acetate) ion-exchange resin, with an elutant of 40 ml deionized water followed by 40 ml 85% methanol in water. the product of interest, eluting from the column within the first 40 ml volume, is dried in vacuo, dissolved in 2 ml of methanol which is cooled in an ice bath. The methanol solution is treated with 30 ml of cold ether, producing thereby a precipitate. The ether is decanted and the residue is dried in vacuo to yield $N^\alpha$-[3-methyl-2-(3-phenyl-2-benzamidothiopropyl) butanoyl]-L-arginyl-p-nitroanilide acetic acid salt.

EXAMPLE IX $N^\epsilon$-benzyloxycarbonyl-L-lysyl-p-nitroanilide hydrochloride In a round bottom flask suitable for vacuum, 0.35 g of $N^\alpha$-t-butoxycarbonyl-$N^\epsilon$-benzyloxycarbonyl-L-lysyl-p-nitroaniline (as described in U.S. Pat. No. 3,884,896) is treated with 4 ml of 4 molar hydrogen chloride in anhydrous dioxane for one hour at room temperature, followed by evaporation in vacuo to a residue. The residue is washed with anhydrous ether, and then dried in vacuo. The resulting product is $N^\epsilon$-benzyloxycarbonyl-L-lysyl-p-nitroanilide hydrochloride.

EXAMPLE X $N^\Delta$-benzyloxycarbonyl-l-ornithyl-p-nitroanilide hydrochloride Following the procedure in Example IX, replacing $N^\alpha$-t-butoxycarbonyl-$N^\epsilon$-benzyloxycarbonyl-L-lysyl-p-nitroanilide with $N^\Delta$-t-butoxycarbonyl-$N^\Delta$-benzyloxycarbonyl-L-ornithyl-p-nitroaniline produces the product $N^\Delta$-benzyloxycarbonyl-L-ornithyl-p-nitroaniline hydrochloride.

EXAMPLE XI $N^\alpha$-[3-methyl-3-(3-phenyl-2-benzamidothiopropyl)butanoyl-$N^\epsilon$-benzyloxycarbonyl]-L-lysyl-p-nitroanilide Following the procedure in Example VII replacing $N^\omega$-(4-methoxybenzenesulfonyl)-L-arginyl-p-nitroanilide hydrobromide with $N^\epsilon$-benzyloxycarbonyl-L-lysyl-p-nitroanilide hdyrochloride provides $N^\alpha$-[3-methyl-2-(3-phenyl-2-benzamidothiopropyl)butanoyl]-$N^\epsilon$-benzyloxycarbonyl-L-lysyl-p-nitroanilide.

EXAMPLE II $N^\alpha$-[3-methyl-2-(3phenyl-2-benzamidothiopropyl)-butanoyl]-$N^\Delta$-benzyloxycarbonyl-L-ornithyl-p-nitroanilide Following the procedure in Example VII replacing $N^\omega$-(4-methoxybenzenesulfonyl)-L-arginyl-p-nitroanilide hydrobromide with $N^\Delta$-benzyloxycarbonyl-L-ornithyl-p-nitroanilide hdyrobromide provides $N^\alpha$-[3-methyl-2-(3-phenyl-2-benzamidothiopropyl-butanoyl]-$N^\Delta$-benzyloxycarbonyl-L-ornithyl-p-nitroanilide.

EXAMPLE XIII $N^\alpha$-[3-methyl-2-(3-phenyl-2-benzamidothiopropyl)-butanoyl]-L-lysyl-p-nitroanilide hydrobromide Cleavage of the benzyloxycarbonyl protecting group from $N^\alpha$-[3-methyl-2-(3-phenyl-2-benzamidothiopropyl)butanoyl]-$N^\epsilon$-benzyloxycarbonyl-L-lysyl-p-nitroanilide with 30% hydrobromic acid in acetic acid as described in Example V provides $N^\alpha$-[3-methyl-2-(3-phenyl-2-benzamidothiopropyl)butanoyl]-L-lysyl-p-nitroanilide hydrobromide.

EXAMPLE IX $N^\alpha$-[3-methyl-2-(3-phenyl-2-benzamidothiopropyl)-butanoyl]-L-ornithyl-p-nitroanilide hydrobromide Cleavage of the benzyloxycarbonyl protecting group from $N^\alpha$-[3-methyl-2-(3-phenyl-2-benzamidothiopropyl)butanoyl]-$N^\Delta$-benzyloxycarbonyl-L-ornithyl-p-nitroanilide with 30% hydrobromic acid in acetic acid as described in Example V provides $N^\alpha$-[3-methyl-2-(3-phenyl-2-benzamidothiopropyl) butanoyl]-L-ornithyl-p-nitroanilide hydrobromide.

What we claim is:

1. A compound of the formula

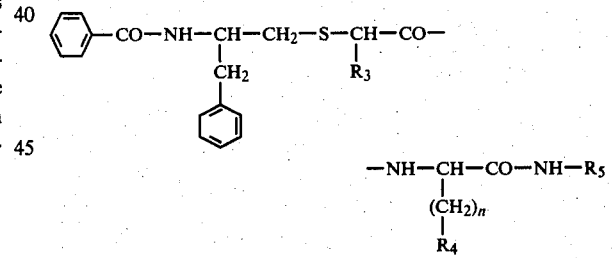

and the biologically acceptable acid addition salts thereof wherein $R_3$ represents an alkyl having 1–6 carbon atoms; $R_4$ represents amino or guanidino; $R_5$ represents p-nitrophenyl, methylnitrophenyl, dinitrophenyl, naphthyl, or nitronaphthyl; and n is 3 or 4.

2. A compound of the formula

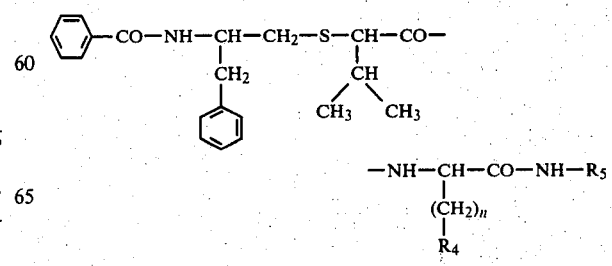

and the biologically acceptable acid addition salts thereof wherein $R_4$ represents amino or guanidino; $R_5$ represents p-nitrophenyl, methylnitrophenyl, dinitrophenyl, naphthyl, or nitronaphthyl; and n is 3 or 4.

3. The biologically acceptable acid addition salts of a compound of the formula

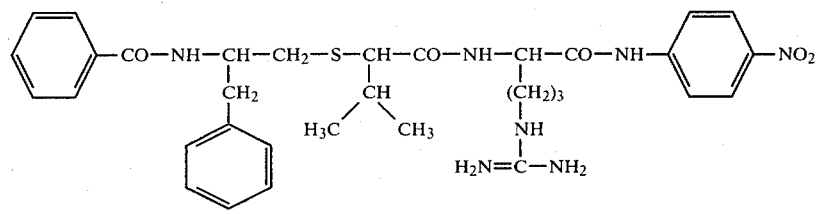

4. A compound according to claim 3 which is $N^\alpha$-[3-methyl-2-(2-phenyl-2-benzamidothiopropyl)butanoyl]-L-arginyl-p-nitroaniide acetic acid salt.

* * * * *